United States Patent [19]
Swiderek et al.

[11] Patent Number: 5,932,473
[45] Date of Patent: Aug. 3, 1999

[54] PREPARATION OF A CELL CULTURE SUBSTRATE COATED WITH POLY-D-LYSINE

[75] Inventors: Mark S. Swiderek, Gloucester; Frank J. Mannuzza, Burlington; Stephen R. Ilsley, Boston; Arthur Myles, Acton, all of Mass.

[73] Assignee: Becton Dickinson and Company, Franklin Lakes, N.J.

[21] Appl. No.: 08/941,473

[22] Filed: Sep. 30, 1997

[51] Int. Cl.$^6$ .............................. C12M 3/00; C12N 11/00; C12N 11/08; C12N 5/00
[52] U.S. Cl. ..................... 435/289.1; 435/174; 435/176; 435/177; 435/180; 435/395; 435/402
[58] Field of Search ..................................... 435/174, 177, 435/176, 395, 402, 289.1

[56] References Cited

U.S. PATENT DOCUMENTS 5,741,701  4/1998  Smiderek et al. ................... 435/297.1

*Primary Examiner*—David M. Naff
*Attorney, Agent, or Firm*—Bruce S. Weintraub, Esq.

[57] ABSTRACT

A cell culture substrate is coated with a composition containing a cell adhesion promoter in a salt solution. A substrate such as plastic, glass or microporous fibers is coated with a composition containing about 5 $\mu$g/ml to about 1000 $\mu$g/ml of poly-D-lysine in an 0.005 M to about 0.5 M citrate or sulfate salt solution to provide about 50 $\mu$l to about 500 $\mu$l of the composition per cm$^2$ of substrate, and the coated substrate is rinsed to remove extraneous materials and dried to obtain a coated substrate having increased shelf-life and/or stability. The coated substrate may be sterilized by rinsing with a sterilizing medium such as ethanol.

9 Claims, No Drawings

PREPARATION OF A CELL CULTURE SUBSTRATE COATED WITH POLY-D-LYSINE

FIELD OF THE INVENTION

The present invention relates to a method for increasing the stability and/or shelf-life of a variety of coated substrates, such as, for example, cell adhesion coated substrates wherein this method involves utilizing an improved coating composition for application to the surface of a substrate.

BACKGROUND OF THE INVENTION

The harvest of cells from tissue for maintenance and propagation in vitro by tissue culture is a major tool in medical and biochemical research. Tissue culture is the technique or process of propagating and/or supporting the metabolism of tissues or cells derived from organisms (plant or animal) in a formulated nutritive environment. Once isolated by gentle tissue dissociation, cells are incubated in nutritive media capable of supporting life functions. With few exceptions, cells require attachment to a substratum in order to perform normal metabolic functions, grow and divide. In tissue, the substratum which provides the support for cell growth is either the basement membrane or interstitial matrix which consists of collagen, laminin, fibronectin, etc. In vitro, this substratum is most often plastic, although glass and microporous cellulosic and other filters are sometimes used as substitutes. Examples of cell uses produced via tissue culture include: (1) the study of the metabolism of the cell, the effect of infectious agents (i.e., viruses, bacteria, etc.) on the cell, the interactive metabolism of different cell types (i.e., epithelial cells, fibroblasts, immuno-competent cells, thymocytes, platelets, etc.), the effect of exogenous factors on cellular metabolism, the genetic composition of cells (in vitro diagnostics); (2) the production of specific compounds, i.e., DNA, RNA, proteins or other cellular components; and (3) the re-implantation of cells as for skin, corneal grafts, brain, vascular grafts, and in vitro fertilization.

In recent years, collagen, laminin, fibronectin and other extracellular matrix components have been extracted and purified from animal tissues and marketed to cell and tissue culture researchers as cellular adhesion promoters. Synthetic poly-D-lysine and poly-L-lysine have also been sold for such purposes. The primary reason for this is that, in vitro, substrates such as plastic or glass are biologically inert and often do not provide sufficient substrate adhesion for adequate cell or tissue attachment. Specific examples illustrative of poor attachment efficiency include primary cell isolates, cells seeded at low densities, transfected cells, and cells seeded in continuous flow systems such as bio-reactors or hollow tube culture systems. In addition, certain substrates such as some microporous filters or Teflon® materials used for vascular grafts do not permit any cell attachment due to low surface energy.

Although cell adhesion promoters have assisted with attachment problems to a significant degree, certain inadequacies are still noteworthy. In particular, once attached to the substrate, most of these factors have a variable and inadequate shelf life.

It is, thus, one object of the present invention to provide coating compositions useful as cell adhesion promoters and stabilizers to facilitate or augment attachment efficiency, rate and/or strength of adhesion, growth and specialized function of cells to tissue culture or nontissue culture materials and substrates including plastic, glass, metals, microporous filters (cellulosic, nylon, glass fiber, polyester, polycarbonate, polyethylene terephthalate and other synthetic and nonsynthetic materials including other synthetic polymeric materials and products resulting from modifications made to the aforementioned synthetic polymeric materials), natural polymers or other nonsynthetic materials, and synthetic or alloplastic materials that may be used in tissue or prosthetic graft procedures (e.g., mechanical heart and polytetrafluoroethylene and related vascular grafting materials).

A second object of the present invention is to provide preparations useful as cell adhesion promoters to facilitate or augment attachment efficiency, rate and/or strength of adhesion of other biologically active moieties such as proteins, DNA, hormones and antibiotics to a variety of substrates, some of which are mentioned above.

Thus biologically active moieties such as proteins and other macromolecules can be coated onto substrate surfaces such as, for example, polystyrene surfaces, by noncovalent adsorption from aqueous solutions. The amount of these macromolecules absorbed onto such surfaces depends on the coating conditions (such as, for example, pH, temperature, ionic strength, ionic composition, concentration of reactants, etc.). The stability of the coating on the surface also depends on similar parameters, as well as the extent of the dryness of the coating and storage conditions (such as, for example, humidity, temperature, gaseous environment, etc.).

The inventors have found that the stability of poly-D-lysine coated surfaces strongly depends on the counter anion that is used during the coating process. Poly-D-lysine is very highly positively charged at neutral pH, and is therefore complexed with a counter anion on the coated surface. It has been found that by applying an improved coating composition of the present invention, such as, for example, a coating composition comprising poly-D-lysine in a citrate or sulfate solution (thus using citrate salt or sulfate salt as the counter anion), to various substrate surfaces, this will result in an increased shelf-life for these substrates. The results obtained are far superior to previous coating compositions which use chloride, acetate, EDTA, carbonate and PBS (phosphate/chloride combination) solution or water.

The present PDL BIOCOAT® Cellware product which is PDL in 1×PBS solution coated onto polystyrene surfaces, has a shelf-life that is dependent on the configuration of the substrate (whether it is a dish, flask or plate, as well as the size and number of cavities in the plates), storage temperature, humidity, packaging, etc. The shelf-life (i.e., stability) of a coated substrate can be enhanced at least two to three-fold by the method of the present invention.

The method of the present invention can be utilized to coat a variety of substrates, as described above and including, for example, plasticware, to increase the shelf-life of such products and allow room temperature storage for such products instead of requiring refrigeration at, for example, 4° C. or lower temperatures. The method of the present invention results in a stability/increased shelf-life which is not dependent on the packaging of, for example, the plasticware.

SUMMARY OF THE INVENTION

The present invention relates to a method for increasing the shelf-life and/or stability of a variety of coated substrates, such as cell adhesion coated substrates, wherein this method includes applying an improved coating composition to a substrate surface, wherein this coating composition consists of a cell adhesion promoter in a salt solution, the salt being, for example, a citrate salt or sulfate salt.

The present invention relates to a method for increasing the shelf-life and/or stability of a coated substrate comprising:

(a) coating a substrate with a coating composition comprising 5 µg to 1000 µg of a cell adhesion promoter in an about 0.005 M to about 0.5 M salt solution;

(b) incubating the coating composition on the substrate;

(c) rinsing the coated substrate to remove extraneous materials not firmly attached to the substrate;

(d) drying the substrate with the coating composition thereon; and (e) obtaining a coated substrate with increased shelf-life and/or stability.

The coated substrate obtained from the method of the present invention has increased shelf-life and/or stability at room temperature. There is no need for special packaging for the coated substrate.

DETAILED DESCRIPTION OF THE INVENTION

The present invention is directed to a method for increasing the shelf-life and/or stability of various coated substrates such as cell adhesion coated substrates. A critical aspect of the method of the present invention is the preparation and utilization of an improved coating composition which is applied to the substrate surface and results in a surface which has improved stability and increased shelf-life. This coating composition is comprised of a cell adhesion promoter in a salt solution.

The present invention relates to a method for increasing the shelf-life and/or stability of a coated substrate comprising:

(a) coating a substrate with a coating composition comprising 5 µg to 1000 µg of a cell adhesion promoter in an about 0.005 M to about 0.5 M salt solution;

(b) incubating the coating composition on the substrate;

(c) rinsing the coated substrate to remove extraneous materials not firmly attached to the substrate;

(d) drying the substrate with the coating composition thereon; and (e) obtaining a coated substrate with increased shelf-life and/or stability.

The substrate can be coated with from about 50 ul to about 500 ul of said composition per $cm^2$ of substrate containing from about 5 ug/ml to about 1000 ug/ml of cell adhesion promoter.

In a preferred embodiment, the coating composition consists of poly-D-lysine as the cell adhesion promoter in a salt solution. Preferably the salt can be a citrate salt or a sulfate salt. In another embodiment, the cell adhesion promoter can be selected from poly-L-lysine, collagen, laminin, fibronectin, polyornithine (polyamino acid) or other cell adhesion substances or mixtures thereof. Although the preferred embodiment of the salt solution herein is a citrate or sulfate salt solution as further described below, the salt solution utilized in the present invention can be any salt solution which can accomplish the goals of the present invention and can include boric acid; salts of dicarboxylic acids; such as succinic, tartaric and glutaric acid; zwitterionic sulfonic acid salts; and organic buffers such as MES (2[N-morpholino]ethanesulfonic acid), bis-tris (bis[2-hydroxyethyl)iminotris[hydroxymethyl]methane), MOPS (3-[N-morpholino]propanesulfonic acid), and HEPES (N-[2-hydroxyethyl]piperazine-N'-[2-ethanesulfonic acid]).

Substrates for conventional cell culture research include plastic, glass, and microporous filters (e.g., cellulosic, nylon, glass fiber, polyester, polycarbonate). Substrates for bioreactors used in batch or continuous cell culture or in genetic engineering include hollow fiber tubes or microcarrier beads. Substrates for vascular or bone grafts include materials such as polytetrafluoroethylene (Teflon®), ceramics and related polymeric materials. Most of these surfaces carry a net negative charge and, therefore, tend to bind tightly net positively charged materials.

The growth and normal metabolism of eukaryotic cells requires attachment to a substrate. Conventionally, cell culture utilizes plastic substrates and, to a lesser degree, glass and microporous filters for cell attachment and propagation. More recently, physiological substances (collagen, laminin, fibronectin, poly-D-lysine and poly-L-lysine) have been utilized for these purposes coated onto plastic (polystyrene) to avoid problems inherent in the culture of transfected cells, transformed cells, primary cell isolates or cells seeded at low seeding densities.

Preferred substrate configurations contemplated by the present invention include multiwell plates (such as 24-well and 96-well plates), dishes (such as petri dishes), culture flasks, etc.

The coating of substrates with the improved coating composition of the present invention and attachment to substrates is generally performed as follows. Depending on the final concentration desired, about 0.5 to 2.0 ml of the coating composition is applied to a well in a 6-well multiwell plate; about 0.25 to 1.0 ml is applied to a well in a 24-well multiwell plate; and about 50 µl to 100 µl is applied to a well in a 96-well plate. Furthermore, in, for example, dishes, about 0.5 to 2.0 ml is applied to a 35 mm dish, 0.5 to 4.0 ml is applied to a 60 mm dish and 2.0 to 12.0 ml is applied to 100 mm dish.

After application, the coating composition is incubated to permit adsorption of the cell adhesion substance(s) to the substrate surface; the remaining coating composition is then removed; the coated substrate surface is then rinsed to remove any extraneous materials; then dried; and, finally, a stable coated substrate with an increased shelf life is obtained.

The coated substrate surface can be rinsed with for example, water, ethanol or any medium which is a biologically compatible sterilizing medium.

In another embodiment, the present invention relates to an in vitro cell culturing system comprising: a substrate; a coating thereon of a coating composition comprising about 5 µg/ml to 1000 µg/ml of an adhesion promoter in about 0.005 M to about 0.5 M salt solution. The substrate, coating composition, adhesion promoter, and salt solution can be any as defined above.

The following examples are for illustrative purposes and are not intended to in any way limit the embodiments of the present invention.

EXAMPLE 1

A rat cerebellar granulocyte assay was carried out in coated multiwell plates having 96 wells, previously stored under accelerated stability conditions at 50° C. saturated humidity and 50° C. ambient humidity; plates held at 4° C. as controls were tested.

The assay was performed in three separate multiwell plates, each coated with the coating compositions described below: (1) a multiwell plate coated with poly-D-lysine in citrate solution; (2) a multiwell plate coated with poly-D-lysine in sulfate solution; and (3) a multiwell plate coated with poly-D-lysine in PBS solution.

These plates were prepared as follows.

(1) Poly-D-lysine was dissolved in 0.1 M sodium citrate solution with 5 mM Tris base adjusted to pH 8.0 to a final concentration of 50 ug/ml. About 80 ul/well of this coating composition was added to the 96-well plate. The coating composition was allowed to adsorb to the surface of the plate for about one hour. Any remaining coating composition was vigorously decanted. Then water was added to the wells at two times the previous volume (of the coating composition) and removed. This step was then repeated. Then the plate was dried in a vacuum oven at room temperature overnight. The plate was then passed through an ultraviolet tunnel.

(2) Poly-D-lysine was dissolved in 100 mM sulfate solution with 5 mM Tris, pH 8.0 to a final concentration of 50 ug/ml.

The same coating process as in (1) was carried out in (2).

(3) Poly-D-lysine was dissolved in 1×PBS solution adjusted to pH 8.0 to a final concentration of 50 ug/ml. (1×PBS=2.7 mM KCl; 1.5 mM $KH_2PO_4$; 137 mM NaCl; 3.7 mM $Na_2HPO_4$)

The same coating process as in (1) and (2) was carried out in (3).

The rat cerebellar granulocyte (RCG) assay for assessing the quality of coating compositions was based on the cell attachment of primary cultures of RCG cells, and was carried out as follows.

RAT CEREBELLAR GRANULOCYTE ATTACHMENT ASSAY 1.0 Cell Isolation

RCGs were isolated from rat cerebellum as follows.

This procedure describes isolation of cells from 6 (and 12) pairs of rat cerebella. Volumes of reagents were adjusted proportionately if fewer than or more than 6 (and 12) pair of cerebella were used.

1.1 Materials 1.1.1 Rat cerebella from 6–12 day old pups, 6 pair (12 pair)

1.1.2 Trypan blue, P/N 01-06090

1.1.3 0.2 micron Nalgene vacuum filter, P/N 01-00048

1.1.4 Millex GV filters, P/N 01-00052

1.1.5 Current lot of Solution 1 (HEPES [N-2-Hydroxy ethylpiperazine-N'-2-Ethane sulfonic acid]containing culture medium)

1.1.6 Trysin Stock Solution, 10 mg/ml 1.1.7 DNAse Stock Solution 1.1.8 Soybean Trypsin Inhibitor stock solution, 3.5 mg/ml 1.1.9 0.5 M $MgSo_4$ Stock Solution 1.1.10 0.05 M $CaCl_2$ Stock Solution 1.1.11 Rat Cerebellar Granule Cell Growth Medium.

1.2 Equipment 1.2.1 Inverted microscope, Equipment ID C-00043

1.2.2 Hemacytomer 1.2.3 Tabletop centrifuge, Equipment ID C-00468 or C-00012

1.2.4 Laminar flow hood, Equipment ID C-00018 or C-00019

1.2.5 Incubator, 5% $CO_2$, 37° C., Equipment ID C-00016 or C-00465

1.3 Supplies 1.3.1 Centrifuge tubes, 15 ml, P/N 01-00018

1.3.2 Centrifuge tubes, 50 ml, P/N 01-00013

1.3.3 1 ml pipette, P/N 01-00042

1.3.4 5 ml pipette, P/N 01-00044

1.3.5 10 ml pipette, P/N 01-00041

1.3.6 25 ml pipette, P/N 01-00040

1.3.7 100 mm Petri dish, P/N 01-03003

1.3.8 Cell scraper, disposable, CoStar C/N 3010

1.3.9 Liter sterile bottle 1.3.10 Syringes

| | Number of Syringes Needed | |
|---|---|---|
| Syringe | 6 Pair Cerebella Preparation | 12 Pair Cerebella Preparation |
| 10 ml | 1 | N/A |
| 30 ml | 2 | 1 |
| 60 ml | 1 | 3 |

1.4 Preparation of Solutions

NOTE: All values and information in parentheses apply to preparation of 12 pairs of rat pup cerebella.

NOTE: All solutions were used within 24 hours of date and time of preparation.

1.4.1 All solutions were prepared under the laminar flow hood.

1.4.2 The following solutions were thawed in a 37° C. water bath and stored in a 4° C. refrigerator until needed:

| Solution Medium | Amount to Thaw | For Preparing |
|---|---|---|
| Trypsin | 1 tube (2 tubes) | Solution 2 |
| DNAse Stock | 2 tubes (4 tubes) | Solutions 3 and 4 |
| STI Stock | 2 tubes (4 tubes) | Solutions 3 and 4 |

1.4.3 Preparing Solution 2 (trypsin solution)

1.4.3.1 35 ml of Solution 1 was transferred into each of two sterile 50 ml centrifuge tubes.

1.4.3.2 0.875 ml of trypsin stock solution was added to each 50 ml tube.

1.4.3.3 The tubes were capped and mixed by inversion or vortex.

1.4.3.4 A 60 ml syringe and a Millex GV 0.22 $\mu$m filter were used to sterile filter each tube of solution into a new, sterile 50 ml centrifuge tube(s).

1.4.3.5 The resulting tube(s) of Solution 2 were reserved for later use.

1.4.4 Preparing Solution 3 (DNAse and STI solutions)

1.4.4.1 20 ml of Solution 1 was transferred into each of two sterile 50 ml centrifuge tubes.

1.4.4.2 0.95 ml of DNAse stock solution was added to each tube.

1.4.4.3 0.94 ml of STI stock solution was added to each tube.

1.4.4.4 22 $\mu$l of 0.5 M $MgSO_4$ stock solution was added to each tube.

1.4.4.5 Each tube was capped and mixed by inversion or vortex.

1.4.4.6 A 30 ml syringe and a Millex GV 0.22 $\mu$m filter were used to sterile filter the tubes of solution into new, sterile 15 ml centrifuge tubes.

1.4.4.7 The resulting tubes of Solution 3 were reserved for later use.

1.4.5 Preparing Solution 4 (DNAse and STI Solutions)
 1.4.5.1 5 ml of Solution 1 was transferred into each of two sterile 15 ml centrifuge tubes.
 1.4.5.2 0.57 ml of DNAse stock solution was added to each tube.
 1.4.5.3 0.734 ml of STI stock solution was added to each tube.
 1.4.5.4 30 μl of 0.5 M $MgSO_4$ stock solution was added to each tube.
 1.4.5.5 Each tube was capped and mixed by inversion or vortex.
 1.4.5.6 A 10 ml syringe and a Millex GV 0.22 μm filter were used to sterile filter the tube of solution into new, sterile 50 ml centrifuge tubes.
 1.4.5.7 The resulting tubes of Solution 4 were reserved for later use.

1.4.6 Preparing Solution 5 ($MgSO_4$/$CaCl_2$ solutions)
 1.4.6.1 24 ml of Solution 1 was transferred into each of two sterile 50 ml centrifuge tubes.
 1.4.6.2 62 μl of 0.5 M $MgSO_4$ stock solution was added to each tube.
 1.4.6.3 48 μl of 0.05 M $CaCl_2$ stock solution was added to each tube.
 1.4.6.4 Each tube was capped and mixed by inversion or vortex.
 1.4.6.5 A 30 ml syringe and a Millex GV 0.22 μl filter were used to sterile filter the tube of solution into new, sterile 50 ml centrifuge tubes.
 1.4.6.6 The resulting tubes of Solution 5 were reserved for later use.

1.5 Preparation of Rat Brain Cerebellar Granule Cells 1.5.1 Cell Dispersion (two preparations)
NOTE: Rat cerebella were prepared. They arrived on ice, but were not frozen.
 1.5.1.1 A sterile disposable cell scraper was used to transfer 6 pair of cerebella into a 100 mm Petri dish.
 1.5.1.2 The tissue was gently crushed with the cell scraper with wiping strokes, trapping the tissue between the scraper and dish surface.
 1.5.1.3 The tissue was worked with the scraper until a homogeneous paste was obtained (in 2–3 minutes).
 1.5.1.4 10 ml of Solution 1 was added to the dish, ejecting Solution 1 across the tip of the cell scraper to remove any clinging cerebellar tissue.
 1.5.1.5 The cells were suspended by aspirating and ejecting the suspension with the pipette.
 1.5.1.6 The suspension was aspirated and transferred into a 50 ml sterile centrifuge tube.
 1.5.1.7 Steps 1.5.1.4–1.5.1.6 were repeated two more times to transfer the remaining tissue from the Petri dish to the tube.
 1.5.1.8 This tube was reserved for centrifugation.
 1.5.1.9 When preparing 12 pair of rat cerebella, the remaining 6 pair of cerebella were transferred into the 100 mm Petri dish and steps 1.5.1.2–1.5.1.8 were repeated for these cerebella.
 1.5.1.10 The Petri dish and the original cerebella container were discarded.
 1.5.1.11 The tubes were centrifuged at 1000 rpm for 5 minutes at room temperature.
 1.5.1.12 The supernatant was aspirated and discarded.

1.5.2 Trypsinization and DNAse
 1.5.2.1 30 ml of Solution 2 were added to the cell pellets obtained in Step 1.5.1.
 1.5.2.2 The mixture was dispersed by aspirating and ejecting the cell suspension with a 25 ml pipet.
 1.5.2.3 The tubes were incubated for exactly 15 minutes in a 37° C. $H_2O$ bath.
 1.5.2.4 The incubating tubes were agitated by swirling them by hand every 2–3 minutes.
 1.5.2.5 The tubes were removed from the bath.
 1.5.2.6 Any clumps or a gelatinous mass present in the mixture were dispersed in the mixture by aspirating and ejecting the cell suspension with a 25 ml pipet 2–3 times.
 1.5.2.7 Step 1.5.2.6 was repeated with a 5 ml pipet.
 1.5.2.8 Where no clumps or gelatinous mass were present in the mixture, the mixture was dispersed by aspirating and ejecting the cell suspension with a 5 ml pipet 2–3 times.
 1.5.2.9 15 ml of Solution 3 was added to the tubes and swirled by hand for 30–60 seconds.
 1.5.2.10 The tubes were incubated for exactly 15 minutes in a 37° C. $H_2O$ bath.
 1.5.2.11 The incubating tubes were agitated by swirling them by hand every 2–3 minutes to reduce viscosity.
 1.5.2.12 The tubes were removed from the bath.
 1.5.2.13 The tubes were centrifuged at 1000 rpm for 5 minutes at room temperature.
 1.5.2.14 The supernatant was aspirated and discarded.

1.5.3 Single cell suspension.
 1.5.3.1 A 5 ml pipet was used to add 4 ml of Solution 4 to the cell pellet(s) obtained in Step 1.5.2.
 1.5.3.2 The mixture was dispersed by aspirating and ejecting the cell suspension 40 times with a 5 ml pipet. To avoid generating excessive foam, the mixture was run down the wall of the centrifuge tube.
 1.5.3.3 When preparing 12 rat cerebella, the cells of both tubes were pooled into a single 50 ml centrifuge tube.
 1.5.3.4 10 ml of Solution 5 were added to each cell suspension.
 1.5.3.5 The mixture was dispersed by aspirating and ejecting the tube's contents 5–10 times.
 1.5.3.6 The suspension was allowed to sit undisturbed for exactly 5 minutes.
 1.5.3.7 When large, settled clumps appeared, a 10 ml pipet was used to aspirate the cell suspension above the clumps, and the cell suspension was transferred to a new sterile 50 ml centrifuge tube, and the clumps were discarded.
 1.5.3.8 10 ml of Solution 5 was added to each aspirated cell suspension.
 1.5.3.9 The tube's mixture was agitated by swirling it by hand.
 1.5.3.10 The tube was centrifuged for 5 minutes at 1000 rpm at room temperature.
 1.5.3.11 The supernatant was aspirated and discarded.

1.6 Cell count and viability
1.6.1 The cell pellet was resuspended in 20 ml of Growth Medium.
 1.6.1.1 A 5 ml pipet was used to add 5 ml of Growth Medium to the cell pellet.
 1.6.1.2 The mixture was dispersed by using the 5 ml pipet to aspirate and eject the cell suspension.
 1.6.1.3 15 ml of Growth Medium was added to the cell suspension.
 1.6.1.4 The mixture was dispersed by aspirating and ejecting the cell suspension.
1.6.2 A 1:10 dilution of cells was created by:
 1.6.2.1 Pipeting 0.1 ml of the cell suspension to a sterile 5 ml centrifuge tube.
 1.6.2.2 Adding 0.4 ml of growth medium to the tube.
 1.6.2.3 Adding 0.5 ml of trypan blue to the tube.
1.6.3 The tube's contents were gently swirled by hand to mix.

1.6.4 0.1 ml of the dilution was removed for cell counting.

1.6.5 The 1:10 dilution was injected into a hemacytometer until the hemacytometer was filled.

1.6.6 A 3×3 grid of squares was defined and the viable cells were counted in the four corner squares of that grid.

NOTE: Viable cells appear white and refractile. Non-viable cells appear blue-tinged.

1.6.7 The number of cells in each corner square was recorded and the average was determined by dividing the total cell count by 4.

1.7 Calculating the dilution.

1.7.1 The average cells/ml of solution were calculated by taking the number obtained in Step 1.6.7 and multiplying by $10^5$.

1.7.2 The total volume of cell suspension needed for testing the coated plates was calculated by multiplying the number of plates by a specific volume (volume varies by configuration).

1.7.3 The volume of original cell suspension required to make a $1.0 \times 10^6$ cells/ml solution was calculated by multiplying the total volume (Step 1.7.2) times $1 \times 10^6$ and dividing this result by the average cells/ml (Step 1.7.1).

1.7.4 The volume of growth medium to bring the total volume to that volume calculated in Step 1.7.2 was calculated by subtracting the volume of cells (Step 1.7.3) from the total volume (Step 1.7.2).

1.8 The cell suspension for seeding/plating was made by:

1.8.1 Using a pipet to transfer the volume of cells from the original cell suspension as calculated in Step 1.7.3.

1.8.2 Adding this volume to a T-Flask large enough to hold the volume calculated in Step 1.7.2.

1.8.3 Adding the volume of Growth Medium calculated in Step 1.7.4 to the T-Flask.

1.8.4 Swirling the T-Flask gently by hand to mix the suspension.

2.0 Assay Procedure—96 well plate.

2.1 The cell suspension was adjusted to $1.0 \times 10^6$ cells/ml.

2.2 0.1 ml cells/well were seeded in rows C and D. (There are 12 rows and C and D were picked arbitrarily.)

2.3 Incubation was for 22 to 26 hours at 37 C., 5% $CO_2$ balance air, 100% humidity.

2.4 The wells were scored in each row by at least two individuals skilled in the assay using reference assay calibration photographs as a key.

2.5 The data was recorded, averaged and graphed.

2.6 The positive control has a score of 2.0 or greater and the negative control a score of 0 for a valid assay. The score is on a scale of 1–3.

The results of the RCG assay demonstrate the increased stability of the plate which utilized the coating composition with citrate solution and the plate which utilized the coating composition with sulfate solution.

EXAMPLE II

In this example, the same RCG assay was carried in coated multiwell plates having 24 wells, previously held at 50° C. saturated humidity and 50° C. ambient humidity; plates held at 4° C. as controls were tested. The three multiwell plates having 24 wells were coated with either: (1) Poly-D-lysine in citrate solution; (2) Poly-D-lysine in sulfate solution; or (3) Poly-D-lysine (PDL) in PBS solution.

The coating compositions and the coated plates were prepared by the method described in Example I.

The RCG assay was carried out as in Example I, except that in Step 2.2, 0.5 ml of cells were applied per well in the 24-well plate.

The results of this RCG assay demonstrate the increased stability of the plates having a coating composition with citrate solution or a coating composition with sulfate solution.

EXAMPLE III

In this example, a RCG assay was carried out with twelve types of coating composition on 96 well plates previously held at 50° C. saturated humidity and 50° C. ambient humidity; plates held at 4° C. as controls were tested.

The multiwell plates (96 wells) used in this example were coated with:

(1) PDL in 0.1 M $PO_4$ solution with 5 mM Tris adjusted to pH 8.0; (2) PDL in 0.1 M acetate solution with 5 mM Tris adjusted to pH 8.0; (3) PDL in 0.1 M EDTA solution with 5 mM Tris adjusted to pH 8.0; (4) PDL in 0.1 M NaCl solution with 5 mM Tris adjusted to pH 8.0; (5) PDL in 5 mM Tris solution adjusted to pH 8.0; (6) PDL in 0.1 M carbonate solution with 5 mM Tris adjusted to pH 8.0; (7) PDL in 0.1 M citrate solution with 5 mM Tris adjusted to pH 8.0; (8) PDL in 0.1 M sulfate solution with 5 mM Tris adjusted to pH 8.0; (9) PDL in 1×PBS solution with 5 mM Tris adjusted to pH 8.0; (10) PDL in 1×PBS, 12.5% EtOH; (11) PDL in 1×PBS, 25% EtOH; or (12) PDL in 1×PBS, 50% EtOH.

In each solution, poly-D-lysine was dissolved into the solution to a final concentration of 50 ug/ml.

The coating process was carried out as in Example I and II, except that pipetting was not done manually, it was done by an automated machine.

The RCG assay was carried out as described in Example I.

The results of this RCG assay from Day 7 to Day 56 demonstrate the stability/shelf-life of each of the twelve coated compositions on the plates. The increased shelf-life of the coating composition with citrate solution and the coating composition with sulfate solution are clearly demonstrated by this assay.

What is claimed is:

1. An in vitro cell culturing system comprising: a substrate; and a coating thereon of a coating composition comprising about 5 µg/ml to 1000 µg/ml of poly-D-lysine in about 0.005 M to about 0.5 M salt solution where the salt is selected from the group consisting of citrate salt and sulfate salt.

2. A cell culturing system as defined in claim 1 wherein said substrate is coated with from about 50 µl to about 500 µl of said composition per $cm^2$ of substrate containing from about 5 µg/ml to about 1000 µg/ml of poly-D-lysine.

3. A cell culturing system as defined in claim 1 wherein said substrate is selected from the group consisting of synthetic polymeric materials, glass, metals and microporous filters.

4. A method comprising:

(a) coating a substrate with a coating composition comprising about 5 µg/ml to about 1000 µg/ml of poly-D-lysine in an 0.005 M to about 0.5 M salt solution where the salt is selected from the group consisting of citrate salt and sulfate salt;

(b) incubating said coating composition on said substrate;

(c) rinsing said coated substrate to remove extraneous materials not firmly attached to said substrate;

(b) drying the substrate with the coating composition thereon; and (e) obtaining a coated substrate with increased stability and/or shelf life.

5. The method of claim 4 wherein said substrate is coated with from about 50 $\mu$l to about 500 $\mu$l of said composition per cm$^2$ of substrate containing from about 5 $\mu$g/ml to about 1000 $\mu$g/ml of poly-D-lysine.

6. The method of claim 4 wherein said coating composition is sterilized on said substrate by rinsing said substrate with a biologically compatible sterilizing medium.

7. The method of claim 6 wherein said sterilizing medium is ethanol.

8. The method of claim 4 wherein the coated substrate is rinsed to remove extraneous materials with water or buffer solution.

9. The method of claim 4 wherein said substrate is selected from the group consisting of synthetic polymeric materials, glass, metals, and microporous filters.

\* \* \* \* \*